United States Patent
Baust

(10) Patent No.: US 9,566,105 B2
(45) Date of Patent: Feb. 14, 2017

(54) DUAL THERMAL ABLATION DEVICE AND METHOD OF USE

(71) Applicant: John M. Baust, Owego, NY (US)

(72) Inventor: John M. Baust, Owego, NY (US)

(73) Assignee: CPSI Holdings LLC, Owego, NY (US)

( * ) Notice: Subject to any disclaimer, the term of this patent is extended or adjusted under 35 U.S.C. 154(b) by 439 days.

(21) Appl. No.: 13/761,673

(22) Filed: Feb. 7, 2013

(65) Prior Publication Data

US 2013/0204241 A1  Aug. 8, 2013

Related U.S. Application Data

(60) Provisional application No. 61/595,823, filed on Feb. 7, 2012.

(51) Int. Cl.
| | |
|---|---|
| A61B 18/02 | (2006.01) |
| A61B 18/14 | (2006.01) |
| A61B 18/08 | (2006.01) |
| A61B 18/00 | (2006.01) |
| A61B 18/18 | (2006.01) |
| A61B 18/20 | (2006.01) |

(52) U.S. Cl.
CPC .......... *A61B 18/02* (2013.01); *A61B 18/1477* (2013.01); *A61B 18/082* (2013.01); *A61B 2018/00577* (2013.01); *A61B 2018/00994* (2013.01); *A61B 2018/0293* (2013.01); *A61B 2018/1869* (2013.01); *A61B 2018/2005* (2013.01)

(58) Field of Classification Search
USPC ................. 606/21, 23, 24, 282, 29
See application file for complete search history.

(56) References Cited

U.S. PATENT DOCUMENTS

| | | | |
|---|---|---|---|
| 5,573,535 A * | 11/1996 | Viklund | .......................... 606/51 |
| 7,097,641 B1 | 8/2006 | Arless et al. | |
| 7,393,350 B2 | 7/2008 | Maurice | |
| 7,465,300 B2 | 12/2008 | Arless et al. | |
| 7,540,870 B2 | 6/2009 | Babaev | |
| 7,896,870 B2 | 3/2011 | Arless et al. | |
| 7,951,140 B2 | 5/2011 | Arless et al. | |
| 8,083,732 B2 | 12/2011 | Arless et al. | |
| 8,287,526 B2 | 10/2012 | Arless et al. | |
| 2001/0014802 A1* | 8/2001 | Tu | .......................... A61B 18/02 606/21 |
| 2004/0158237 A1 | 8/2004 | Abboud et al. | |
| 2005/0038422 A1* | 2/2005 | Maurice | .......................... 606/21 |
| 2005/0182393 A1 | 8/2005 | Abboud et al. | |
| 2007/0049999 A1* | 3/2007 | Esch | ................. A61B 18/1492 607/96 |

(Continued)

OTHER PUBLICATIONS

Hines-Peralta, et al., Hybrid Radiofrequency and Cryoablation Device: Preliminary Results in an Animal Model, Oct. 2004, pp. 1111-1120, vol. 15, Issue 10, JVIR, Boston, MA.

*Primary Examiner* — Paula J Stice
(74) *Attorney, Agent, or Firm* — Hoffman Warnick, LLC

(57) ABSTRACT

The invention is a multi-functional ablation device that encompasses the use of both heat energy and cryogenic energy as integrated into one medical device. In one embodiment, the medical device integrates a heat source such as RF or HIFU in combination with a source of cryogenic energy such that the multi-functional ablation device is a dual thermal ablation device capable of utilizing either energy source alone or in combination.

19 Claims, 7 Drawing Sheets

(56) References Cited

U.S. PATENT DOCUMENTS

| | | | |
|---|---|---|---|
| 2008/0051774 A1* | 2/2008 | Ofir | A61B 18/02 606/20 |
| 2008/0114346 A1* | 5/2008 | Levin et al. | 606/23 |
| 2010/0286791 A1* | 11/2010 | Goldsmith | 623/23.7 |
| 2011/0184402 A1* | 7/2011 | Baust et al. | 606/23 |

* cited by examiner

DUAL THERMAL ABLATION DEVICE AND METHOD OF USE

RELATED APPLICATIONS

The present application claims priority to U.S. Provisional Patent Application Ser. No. 61/595,823 filed on Feb. 7, 2012 and titled Dual Thermal Ablation Device and Method of Use, which is incorporated herein by reference in its entirety.

FIELD OF THE INVENTION

The present invention relates generally to the medical technology field and, in particular, to a medical device and method for use in thermal treatments.

BACKGROUND OF THE INVENTION

Tissue ablation can be performed to remove undesired tissue such as cancer cells or may also involve the modification of the tissue without removal, such as to stop electrical propagation through the tissue in patients with a cardiac arrhythmia. Often the ablation is performed by passing energy, such as electrical energy, through one or more electrodes causing the tissue in contact with the electrodes to be heat ablated. Other devices have employed cryoprobes/catheters to freeze the tissue, other probes/catheters employing the use of such energy sources as microwaves and lasers, and high intensity ultrasonic devices mechanically causing a physical abrasion or destruction of the tissue.

The use of heat energy and cryogenic energy in combination has limited practice to date due to several factors including, but not limited to, the relatively new mainstream acceptance and utilization of ablation as a treatment option, as well as the inefficacy in utilizing each source of energy independently. Typically, two distinct thermal probes, one to deliver heat energy and one to deliver cryogenic energy are utilized, each technology having a distinct surgical skill set and approach.

Heat energy is routinely used for treating a myriad of diseases. One mode of heat treatment is radio frequency ablation (RFA). Radio frequency ablation has been used to treat a variety of cancers and cardiac anomalies. For instance, RFA has been effective in treating colorectal liver metastases. This procedure has also been used to treat saphenous vein varicoses. Other studies have shown that RFA can serve as a minimally invasive method for treating liver tumors even though it is recognized that the procedure is difficult to monitor in vivo and the blood vessels serve as a heat sink that makes it difficult to control the target temperature. Another problem using RFA in treating renal tumors is the necessity of repeat ablation to make the process more effective. Radiofrequency ablation has also been used to treat Barrett's esophagus and atrial fibrillation. When used to treat atrial fibrillation, RFA creates a risk of injury to the adjacent tissues such as the esophagus. Therefore, esophageal endoscopy is used to screen patients at risk of esophageal thermal injury after RFA.

Microwave energy has been employed with ablation catheters to try to provide sufficiently deep lesions. Since the penetration of microwaves into tissue has a steep exponential decline, the catheter is brought into close contact with the tissue. Fat, however, continues to be a significant barrier.

High powered lasers have also been applied as an ablative energy source, though have a risk of crater formation at the application. Low energy lasers produce lesions with a depth related to duration of application.

High intensity focal ultrasound (HIFU) has also been utilized since it is capable of penetrating fat and inducing fast lesions at specific depths when focused. Tissue is emulsified with millisecond boiling produced by shock wave heating. This procedure has been used to treat such disease states as cardiac arrhythmias and tumors, among others. The heated zone, however, has intact cells remaining after treatment. The treatment using HIFU also has higher complication rates than RFA when treating atrial fibrillation, halting its use in many countries.

Contrary to heat ablation, cryoablation has been utilized to freeze a target tissue. The cryogenic energy is used for treating similar diseases as targeted with heat energy. Cryoablation is used to treat a host of disease states including, but not limited to, liver tumors, actinic keratoses, breast cancer, colorectal cancer, cervical intraepithelial neoplasia, prostate cancer and atrial fibrillation. The cryogenic energy (i.e. severe cold) has the advantages of avoiding clot formation and being a natural analgesic. Although cryoablation has proven to be a successful ablation therapy, complications with the procedure exist and issues with disease recurrence remain. For example, while trying to reach a designated temperature within a target tissue, the application of freezing temperatures is extended causing overfreeze in surrounding non-targeted tissue. In an argon based system, that means a large portion of the damaged tissue is outside the targeted region. In a liquid nitrogen based system, colder isotherms are achieved throughout the iceball to increase cell death and control destruction of the targeted tissue, but overfreeze may also damage surrounding non-targeted tissue.

Given that both RFA and cryoablation are commonly used for similar procedures, the two modalities have each been evaluated for their respective advantages and disadvantages. For instance, cryoablation creates an iceball that can be easily visualized and has a defined zone; whereas RFA is difficult to visualize and can create variable temperatures especially when adjacent to a heat sink such as blood vessels. Both procedures, however, can result in survival of residual cells that may result in disease recurrence at a later point in time.

Currently, two separate, independently operated medical devices each deliver a single therapy, each having their own technical challenges and applications. Such challenges include use in a dynamic environment such as the operating room, high costs, and lengthy procedural times. Individually, present techniques are inefficient, costly, and lack a concerted effort with technologies that could have collective benefits.

A need exists for a multifunctional catheter and/or probe that utilizes the benefits of current ablative technologies but limits the undesirable effects that each individual procedure creates. The integral device will allow for heat ablation and cryoablation within a single unit for dual ablation procedures. The ablation device and method of use will be less time consuming and more effective than techniques individually utilized to date. The device will facilitate ease of use while providing cost efficient solutions to patient care.

SUMMARY OF THE INVENTION

The present invention applies heat energy and cryogenic energy to a tissue using an integral device. The dual ablation device incorporates sources of heat energy and cryogenic energy into one device to allow for the delivery of heat energy and cryogenic energy to a target tissue site. This enables controlled, real-time application of a dual thermal ablation strategy. The dual thermal ablation system disclosed herein provides for a device and a method of use that is capable of delivering a multitude of therapeutic treatment options, including heat and cold, along with the use of anti-cancer agents, alone or in any combination as desired.

In one embodiment, a multi-functional ablation device comprises a hybrid thermal-cooling system comprising an electrical power supply and a cryogen source; a longitudinal body having a proximal end and a distal end wherein the proximal end includes an outer sheath having an electrical connection contained therein and connected to the electrical power supply, and wherein the distal end is a closed tip with a thermally conductive surface; an ablation zone positioned within the distal end and defined by the thermally conductive surface; a cryogen supply line disposed through the longitudinal body and interconnected with the cryogen source for generating subzero temperatures; a wall having an inner surface and an outer surface such that the inner surface creates a cryogen return lumen surrounding said cryogen supply line and the outer surface creates an insulative lumen between the wall and the outer sheath, the wall extended circumferentially through the longitudinal body; and one or more heating elements disposed within the ablation zone of the distal end and contacting the thermally conductive surface of the closed tip, the heating elements interconnected with the electrical connection of the longitudinal body for generating hyperthermic temperatures; wherein the ablation zone transfers subzero temperatures and hyperthermic temperatures to the thermally conductive surface.

In one embodiment, the ablation zone is an integral unit configured for alternating use of the subzero temperatures and the hyperthermic temperatures. The electrical power supply comprises thermoelectric elements or resistive heating elements, alone or in combination. When the longitudinal body is a handheld device and configured to attach to the cryogen source or to the electrical power supply, an umbilical provides the interconnection. In one aspect, any length of umbilical may be utilized. When the longitudinal body is a portable unit, the cryogen source is a cartridge positioned within the longitudinal body. In the portable unit, the electrical power supply is also incorporated in the longitudinal body.

In the multi-functional ablation device of the invention, the insulative lumen is a vacuum. The insulative lumen may also comprise fiber materials including fiberglass, rock wool, slag wool, cellulose, natural fibers, rigid foam, or sleek foils.

One embodiment of the multi-functional ablation device utilizes a cryogen source that is a gas cryogen. One embodiment of the multi-functional ablation device utilizes a liquid cryogen. Another embodiment of the device utilizes a cryogen source that is a cryogen, liquid or gas, at or above a critical point pressure and cooled to a cryogenic temperature below a critical point temperature. In one embodiment, the cryogenic temperature is more than 10% below the critical point temperature. In another embodiment, the cryogenic temperature is more than 10% above the critical point pressure, alone or in combination with the cryogenic temperature being more than 10% below the critical point temperature.

Embodiments of the invention utilize hyperthermic temperatures in the range of between about +40° C. to about +80° C. or greater; and subzero temperatures in the range of between about −40° C. to −200° C. or colder. One embodiment utilizes subzero temperatures in the range of between about −80° C. to −140° C. or colder, and another utilizes subzero temperatures in the range of between about −160° C. to −196° C. This narrower range may incorporate the use of compressed liquid nitrogen, near critical nitrogen, supercritical nitrogen, or similar states of other cryogens without limitation.

The electrical connections in the device comprise electrical supply wiring for interconnecting with the electrical power supply. One embodiment uses an outer sheath to encapsulate the cryogen source and the electrical power supply. In one embodiment, the longitudinal body is a probe or a catheter.

The hybrid thermal-cooling system of the invention comprises an electrical power supply having at least one of radiofrequency energy, microwave energy, ultrasound energy, laser light energy, or thermoelectric energy; and a cryogen source comprising a thermoelectric module or a cryogenic fluid, wherein the cryogenic fluid is in a pressurized state, compressed liquid state, critical state, near critical state, or supercritical state. The cryogenic fluid may be utilized at a temperature above a critical point temperature also.

A method for performing tissue ablation is disclosed in embodiments of the present invention comprising: a longitudinal body having a proximal end and a distal end wherein the proximal end includes an outer sheath having electrical connections contained therein and wherein the distal end is a closed tip with a thermally conductive surface, the thermally conductive surface defining an ablation zone; providing a hybrid thermal-cooling system comprising an electrical power supply and a cooling source configured for integration with the longitudinal body at the proximal end; designating a tissue site for ablation; positioning the ablation zone of the multi-ablation device at a first position of the tissue site; producing heat energy from the electrical power supply; producing cooling energy from the cooling source; directing the heat energy or the cooling energy through the longitudinal body to the ablation zone for a first time period to damage the tissue site; directing the heat energy or the cooling energy through the longitudinal body to the ablation zone for a second time period to damage the tissue site; and removing the ablation zone of the longitudinal body from the tissue site; wherein the steps of directing the heat energy or the cooling energy for the first time period and the second time period destroy the tissue site alone or in combination.

In one embodiment, the method further comprises a step of repeating the steps of directing the heat energy or the cooling energy for the first time period and the second time period, alone or in combination. The method may further comprise a step of repositioning the ablation zone of the longitudinal body to a second position in the tissue site.

When thermoelectric modules are utilized, the heat energy is formed through a thermoelectric process. When an electric power supply is connected to resistance wires or heater unit by way of electrical supply wiring, the heat energy is formed through a resistive heating process. Electrical wiring extending through the longitudinal body interconnects the energy source with the heating or cooling unit in the ablation zone of the tip.

Cooling energy may be created by a cryogen source including argon, nitrous oxide, carbon dioxide, helium, hydrogen, nitrogen, oxygen, methane, chlorofluorocarbons, hydrochlorofluorocarbons, alcohols, or any combination thereof. Cooling energy may also be created by thermoelectric cooling in a thermoelectric module using a semiconductor pellet soldered to an electrically-conductive material. In one embodiment, during the steps of directing the heat energy or the cooling energy for the first time period and the second time period, a thermoelectric module directs electrical current through at least two dissimilar conductors such that a first flow of current in one direction absorbs heat and a second flow of current in an opposite direction releases heat.

Other embodiments include utilizing the multi-functional ablation device in combination with anti-cancer agents, either simultaneously or as an independent step. During the method of utilizing the multi-functional ablation device, the steps of directing heat energy or cooling energy for the first and second time periods can activate cell pathways to induce apoptosis. Aspects of the invention include performing the steps of directing the heat energy or the cooling energy for the first time period and the second time period sequentially. Where zones of ablation are isolated at the thermally conductive surface, the steps of directing heat energy or the cooling energy for the first time period and the second time period can be performed simultaneously.

An embodiment of the present invention is also a tissue ablation probe comprising: a longitudinal body having a proximal end and a distal end wherein the proximal end includes an outer sheath having electrical connections contained therein and wherein the distal end is a closed tip with a thermally conductive surface, the thermally conductive surface defining an ablation zone; a hybrid thermal-cooling system comprising an electrical power supply connected to the electrical connections of the longitudinal body, and a cooling line positioned within the longitudinal body and interconnected with a cooling source at the proximal end; and a controller, or on/off switch, for selectively distributing heat ablation energy and cryogenic cooling energy; wherein the ablation zone is an integral unitary treatment zone such that the thermally conductive surface absorbs and releases heat to destroy a tissue site. The tissue ablation probe is interconnected at a console where an electric source and cryogen source are present. The tissue ablation probe is also an independent handheld device detachable from the console or an independent unitary ablation device.

Various embodiments of the tissue ablation probe include tips in any number of configurations, any size and material composition. One tip is a needle. Another tip is a wedge. Another tip is a paddle.

BRIEF DESCRIPTION OF THE DRAWINGS

The accompanying drawings, which are incorporated in and constitute a part of this specification, illustrate various embodiments of the present invention, and, together with the description, serve to explain the principles of the invention. The various features are not necessarily drawn to scale. In fact, the dimensions may be arbitrarily increased or decreased for clarity of discussion. In the drawings.

DETAILED DESCRIPTION

Reference will now be made in detail to the present embodiments of the invention, examples of which are illustrated in the accompanying drawings. Wherever possible, the same reference numbers will be used throughout the drawings to refer to the same or like parts.

Combination approaches to treat various disease states, including cancer, have moved to the forefront of research and clinical practice. In most cases, combination approaches involve the use of multiple drugs such as anti-cancer agents. Other cases might involve the use of ablation strategies, such as heat energy or cryogenic energy, in combination with anti-cancer agents. The use of heat energy in combination with cryogenic energy provides for an effective combination ablation strategy to target unwanted tissue.

The present invention provides a multi-ablation device that is a probe or catheter having the lethal effects of ablative heat energy and ablative cryogenic energy. The thermal probes and catheters are utilized for performing ablation at a target tissue site in a subject.

Figure 1:
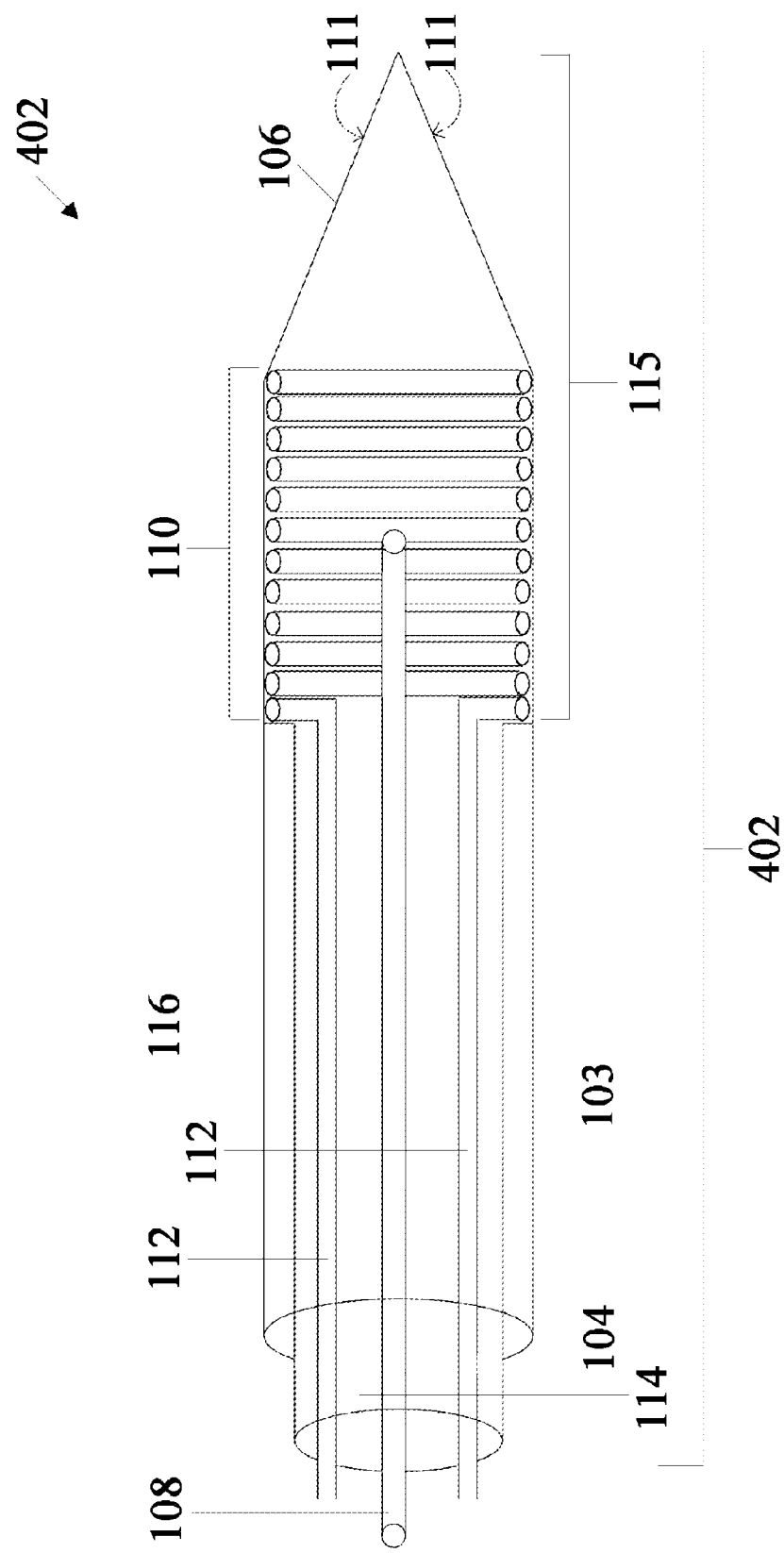
FIG. 1 is an internal side view of an illustrative embodiment of the handheld device in FIG. 4 of the invention.
Figure 2:
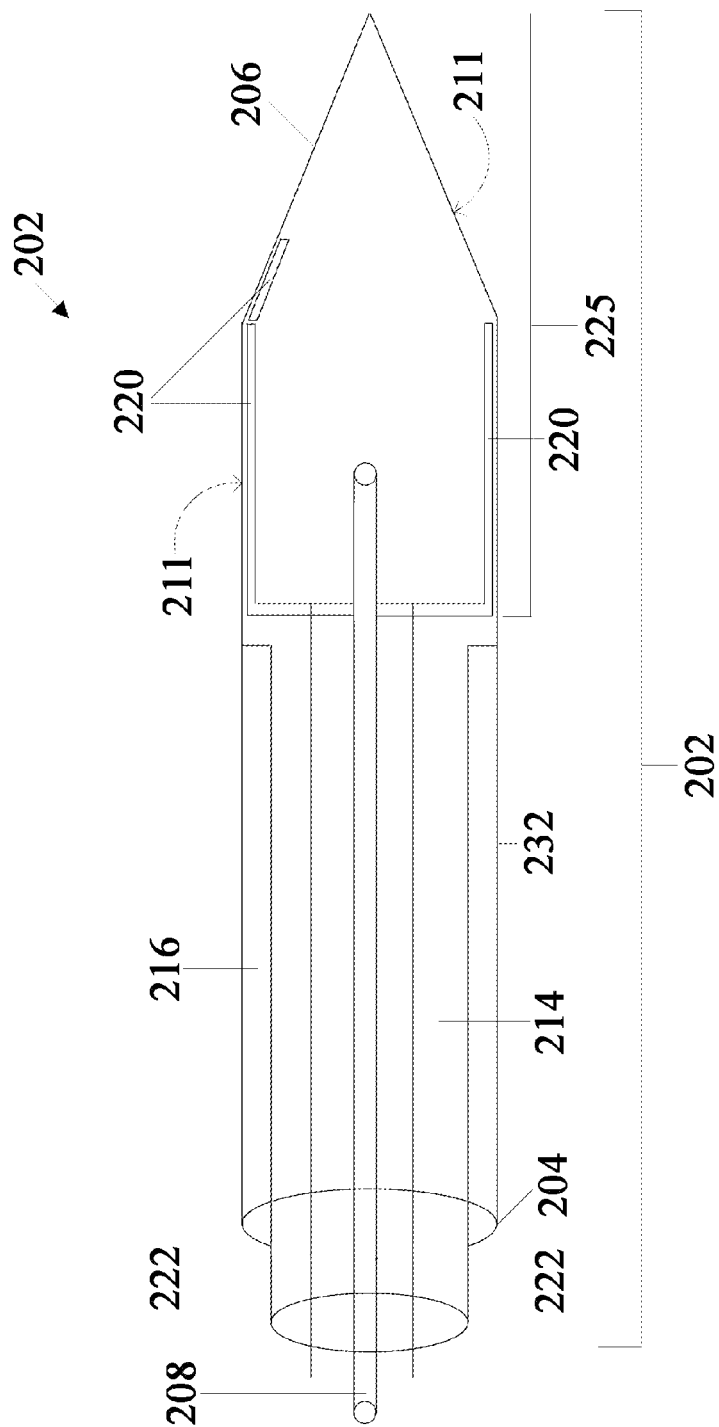
FIG. 2 is an internal depiction of an illustrative embodiment of a device of the invention.
Figure 3:
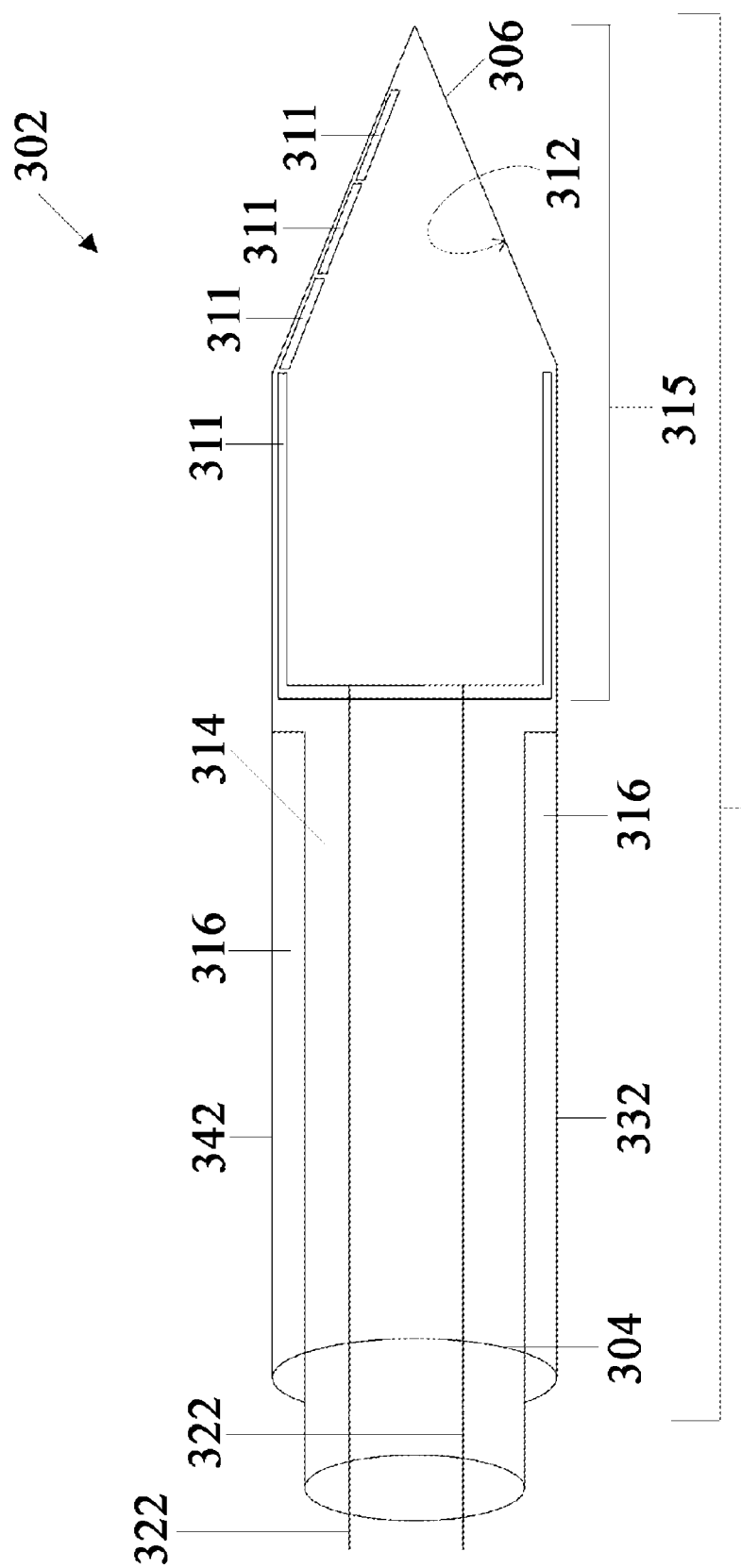
FIG. 3 is an internal side view of an illustrative embodiment of a device of the invention.
Figure 4:
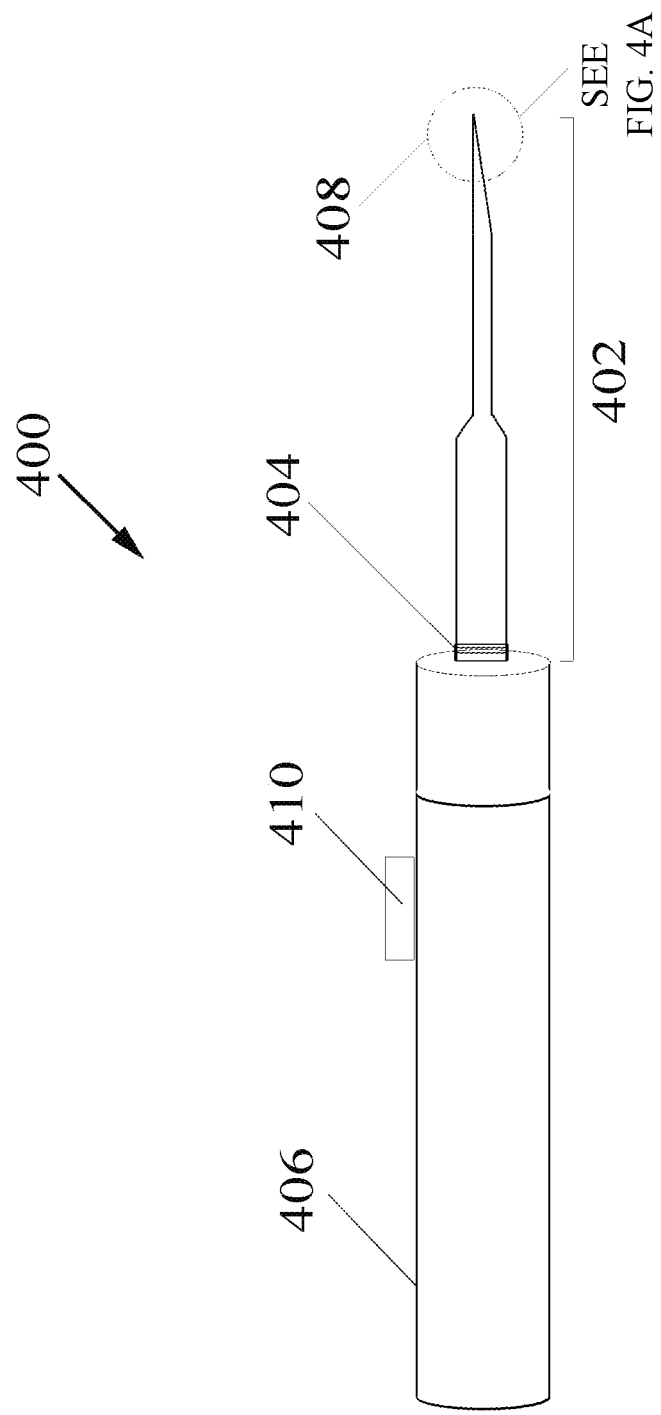
FIG. 4 is an external design of an embodiment of the invention.
Figure 5:
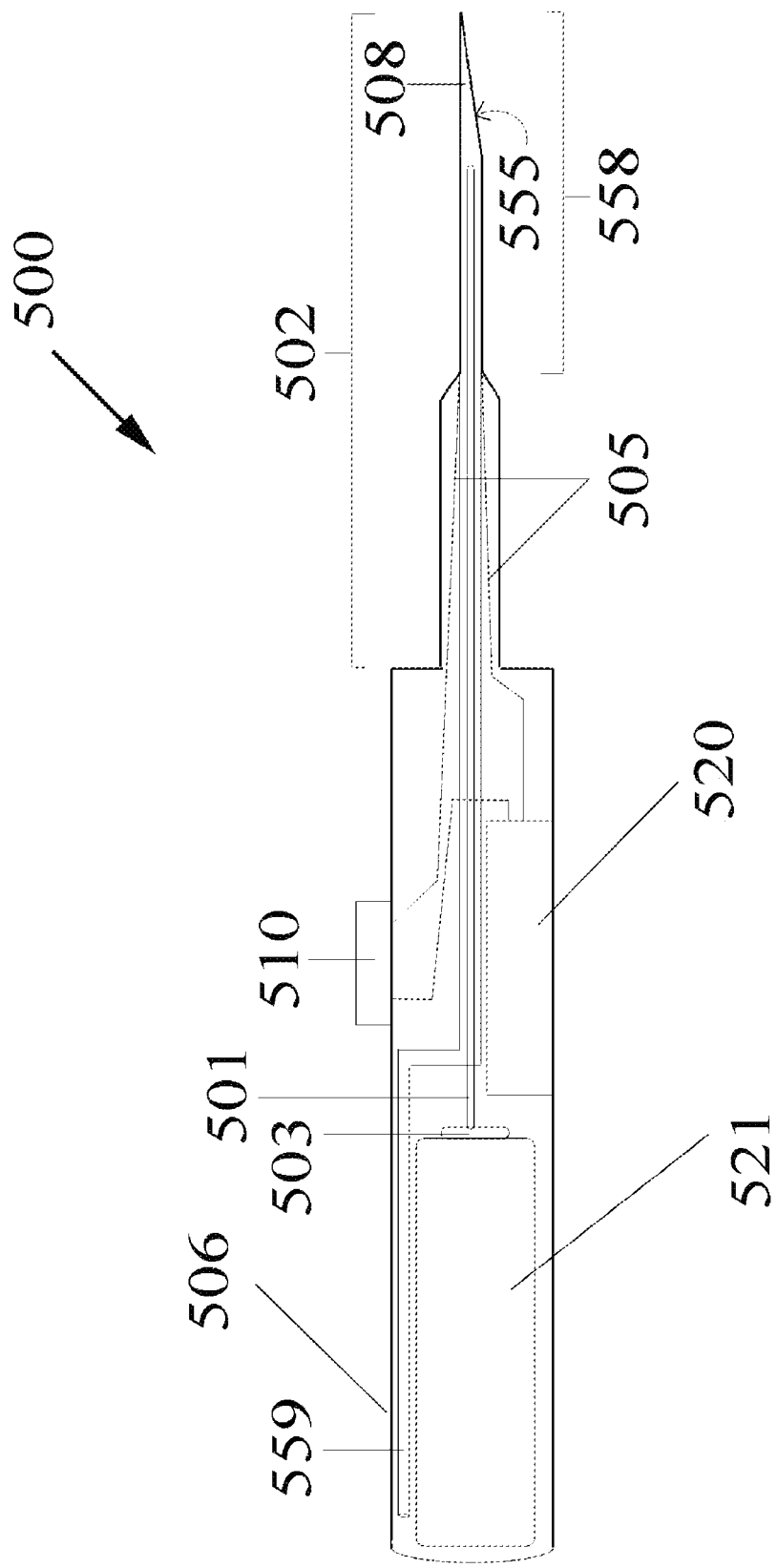
FIG. 5 is an internal view of an embodiment of the handheld invention.

In FIG. 4, an external view of a multi-functional ablation device 400 is illustrated. The device 400 has a longitudinal body 402 with an attachment 404 for connection with a handle 406. Embodiments of the multi-functional ablation device 400 can house different internal components within the longitudinal body 402 as well as different internal components of the handle depending on internal and external energy components. (Various embodiments of the longitudinal body are depicted in FIG. 1, FIG. 2, and FIG. 3.) The handle 406 has an on/off switch 410 to operate the electrical power supply and the cryogen supply units. (As seen in FIG. 5, a handheld unit contains both energy supply units). The on/off switch 410 is a controller for selectively distributing heat ablation energy and cryogenic cooling energy as desired.

Figure 4A:
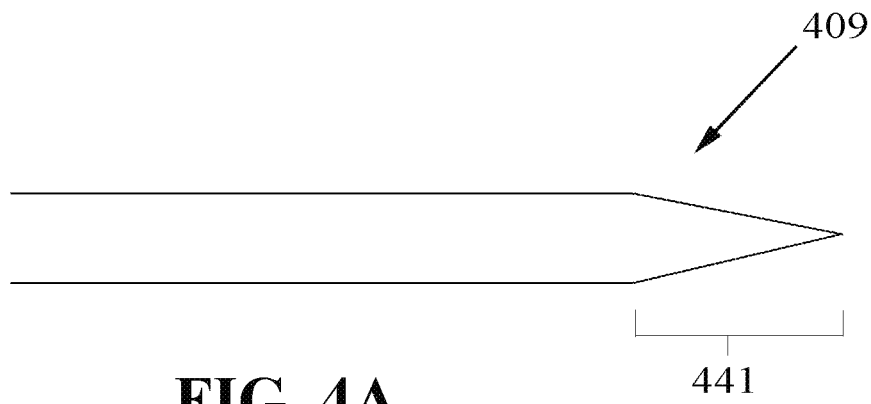
FIGS. 4A, 4B, and 4C depict tip configurations of the invention.
Figure 4B:
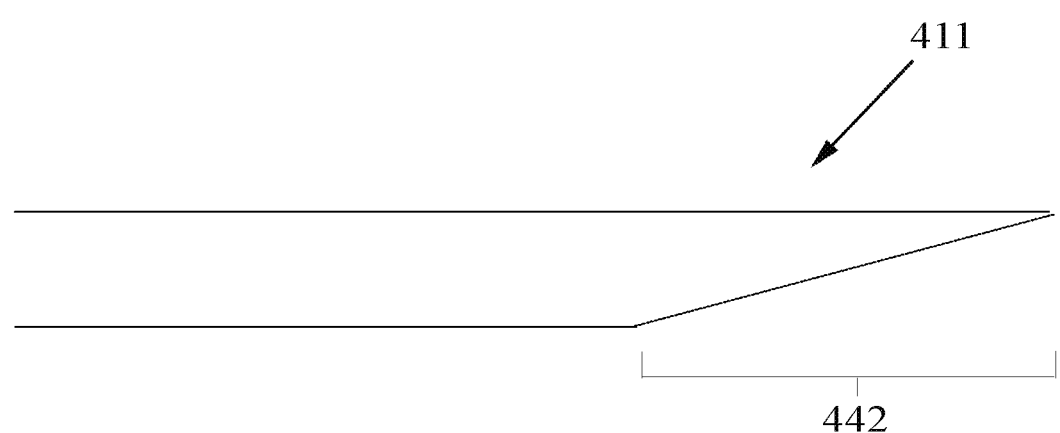
Figure 4C:
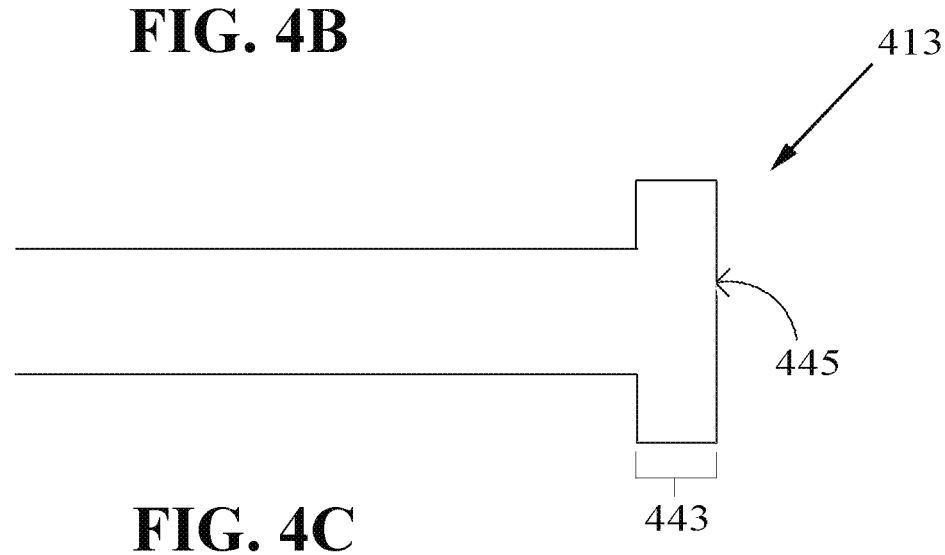

At the distal end of the longitudinal body 402 is a closed tip 408. FIGS. 4A, 4B, and 4C depict three different configurations of a closed tip 408, though any tip maybe utilized as modified in a current design or as currently used with balloon catheters and other probe designs. FIG. 4A illustrates a pointed needle tip 409 for puncturing into a tissue site. The ablation zone 441 is depicted at the distal end. FIG. 4B illustrates a wedge tip 411 for linear ablation such that the wedge tip 411 is placed longitudinally in the tissue to destroy cells along a linear path created by the ablation zone 442. FIG. 4C illustrates a paddle tip 413 creating the ablation zone 443 and having a flat surface 445 for surface ablation. Without limitation, various probe tips may be utilized with the present invention as configured for integration with the longitudinal body or for removable attachment with the longitudinal body. Further, tips allow for customization of the ablation zone to each targeted tissue region.

In the embodiments of the invention, the ablation zone is situated within the distal end and defined by the thermally conductive surface in that the surface that is utilized to transfer heat and/or cold to the tissue site defines a specific size, shape and dimension. For exemplary purposes only and not limitation, a needle probe can be used that has an ablation zone 1.0 cm in length×1.5 mm diameter as created by the thermally conductive surface that surrounds the heating and freezing components; thus, the ablation zone is the three-dimensional treatment zone or may be a twodimensional surface such as a wedge that has one thermally conductive surface defined by a specific length and width. The thermally conductive surface can therefore be formed in various areas on the surface of the closed end tip.

The internal components of the longitudinal body 402 of the dual ablation device 400 are depicted in FIG. 1. In the embodiment depicted, a hollow longitudinal body 402 has an outer sheath 103 with an open end 104 at the proximal end for attachment to an energy source and a closed end tip 106 at the distal end for ablation at the tissue site. At the closed tip 106 is a thermally conductive surface 111 made of stainless steel or other conductive metallic or polymeric material. In the embodiment depicted in FIG. 1, a cryogen gas supply line 108 proceeds through the longitudinal body 402 as inserted at the open end 104 (proximal to a point of attachment) and terminating within the closed end tip 106 (at a distal end). A thermoelectric heater coil 110 is positioned within the closed end tip 106. An electrical connection wire 112 runs through the length of the longitudinal body 402 to direct electrical current to the heater coil 110. The heater coil 110 may include or be replaced with resistance wire to generate heat. Together the thermoelectric heater coil 110 and cryogen supply line 108 in the closed end tip 106 form an ablation zone 115, also referred to herein as the dual ablation zone 115. A return lumen 114 surrounds the supply line 108 and circumferentially extends the length of the longitudinal body 402, allowing the return of gas from the cryogen supply line 108 in the tip 106 back to its source or to be vented into the atmosphere. The vacuum lumen 116 is an insulative lumen 116 that serves as an insulator for the cryogen supply line and electrical connection wires 112. Insulative lumens may also utilize fiber materials including fiberglass, rock wool, slag wool, cellulose, natural fibers, rigid foam, or sleek foils. The open end 104 is integrated with the attachment 404 for interconnection with a handle 406. The open end 104 may also be configured for direct attachment with an umbilical.

In this embodiment, the cryogen gas supply line 108 is a Joule-Thomson cryogen gas supply line 108. In another embodiment the cryogen supply line 108 is a liquid cryogen. Embodiments also integrate various states of cryogen in the supply line 108 such as a cryogen at or above a critical point pressure. In one aspect, the cryogen can then be cooled to a cryogenic temperature below the critical point temperature. Where cryogenic temperatures and pressures are near critical, or more than 10% below the critical point temperature and more than 10% above the critical point pressure, or supercritical, the reduced surface tension of the fluid allows for a reduced friction flow and thereby prevents vapor lock.

In the embodiment of FIG. 1, the multi-functional ablation device has a hybrid thermal-cooling system that operates at hyperthermic temperatures in the range of between about 40° C. to about 80° C. or greater; and the cooling temperatures operate at subzero temperatures in the range of about −40° C. to about −200° C. or colder. In another aspect, temperatures can be utilized between about −80° C. to −140° C. or colder and also in the range of between about −160° C. to about −196° C.

In one aspect, the dual ablation probe 400 is connected to a system comprising a $CO_2$ or $N_2$ gas cartridge system (e.g. 12 g cylinders) in combination with electrical connection wires interconnected with resistance wire or other heating mechanism within the probe. Any number, size and shape of cartridges may be utilized depending on the size and configuration of the handheld device. The configuration illustrated in FIG. 4 delivers effective freezing and/or heating capability to physically destroy cells and to activate cell pathways that induce apoptosis. The heating and freezing in combination works to ablate tissue (a) physically by cryo-destruction and heat-destruction (e.g. thermal radiation, radio frequency energy, ultraviolet light and ionizing radiation); and/or (b) molecularly through apoptotic cell death. FIG. 4 illustrates a handheld device that has a footprint as small as possible and easy to manipulate, though any size and shape of the device may be implemented. In another aspect, the ablation device can be connected to compressed gas systems or energy sources as currently used in the medical industry and in patient care.

FIG. 2 illustrates an embodiment of a longitudinal body 202 such that the thermoelectric heater coil 110 of longitudinal body 402 (from FIG. 4) is replaced with Peltier heater chips 220 in the ablation zone 225 of the closed end tip 206. The closed end tip 206 is formed having a thermally conductive surface 211 that defines the boundaries of the ablation zone 225. The longitudinal body 202 is encompassed by an outer sheath 232 that contains the supply line 208, return lumen 214, and an insulative lumen 216. Electrical connecting wires 222 extend through the longitudinal body 202 to connect and supply power to the Peltier heater chips 220. Together the Peltier heater chips 220 and the cryogen supply line 208 form a dual ablation zone 225. The open end 204 can be integrated with an attachment to affix to a handle or may be configured for connection with an umbilical that interconnects with an external energy source.

Another embodiment of a probe of the present invention is illustrated in FIG. 3 as a hollow longitudinal body 302 surrounded by an outer sheath 332. The longitudinal body 302 has a closed end tip 306 and an open end 304 for attachment to an energy source, hyperthermic, cryogenic or otherwise. A vacuum lumen 316 serves as an insulator between the outer sheath 332 and the open space 314 of the longitudinal body 302. In this embodiment, a series of Peltier heater chips 311 line internal wall 312 of the closed end tip 306. Electric wires 322 extend through the longitudinal body 302 from the open end 304 and connect to the Peltier heater chips 311 at the distal end. The Peltier heater chips 311 in the closed end tip 306 form the ablation zone 315 such that a dual ablation zone 315 is created when the series of Peltier heater chips 311 function in heating and/or cooling the closed end tip 306. The series of miniature Peltier cooling chips are placed and configured within the device to deliver effective ablation temperatures between about 40° C. to about 70° C. or higher and freezing temperatures less than about −40° C. In one aspect, a single Peltier chip is utilized to create a hyperthermic temperature of about 70° C., and provides a cold temperature of about −40° C. when placed in contact with tissue. Heat extraction, however, is not cumulative when multiple chips are utilized.

Calculations of probe performance suggest a string of 4-6 Peltier microchips in the probe tip provide an effective wattage of cooling power to freeze a 1 $cm^3$ volume of tissue to less than about −40° C. Heating of the probe is accomplished via DC current reversal through the Peltier chip, thereby creating heat. As with cooling, DC voltage and various chip cascading/bypass configurations are embodied within the invention to allow for optimal device configuration. Heat calculations suggest that a bypass circuit be integrated into the system as about two to four Peltier chips are utilized to deliver temperatures of about +50° C.

The idea to utilize various approaches to treat various disease states, including cancer, has been realized in combining current ablation treatments. The use of heat energy and cryogenic energy to treat a target tissue enables controlled, real-time application of a dual thermal ablation strategy. Further, the device is capable of delivering a multitude of ablation approaches including freezing, heating, and anti-cancer agents alone or in any combination desired.

FIG. 5 further illustrates the internal components of a handheld device 500. Here, the device is a portable independently operable unit 500. An electrical power source 520 is a battery 520 housed within the handle 506 along with a cryogen source cartridge 521. A cryogen supply line 501 is attached to the cryogen source cartridge 521 through a connector 503 and extends through the longitudinal body 502 to the closed end tip 508. Cryogenic temperatures are transferred to the thermally conductive surface 555 of the ablation zone 558 at the closed end tip 508. A return line 559 allows for the venting of any cryogenic fluid to the atmosphere due to pressure generated at the tip. An electrical connection wire 505 relays electrical energy to the closed end tip 508 where a heating element, e.g. heater coil or Peltier chip (not illustrated), is located to generate hyperthermic temperatures at the thermally conductive surface 555 of the ablation zone 558. An on/off switch 510 controls the delivery of hot or cold temperatures to the probe tip 508. The handheld device 500 may also be configured to interconnect with a console (such as that in FIG. 6) that houses a separate electrical power supply and/or cryogen supply.

Figure 6:
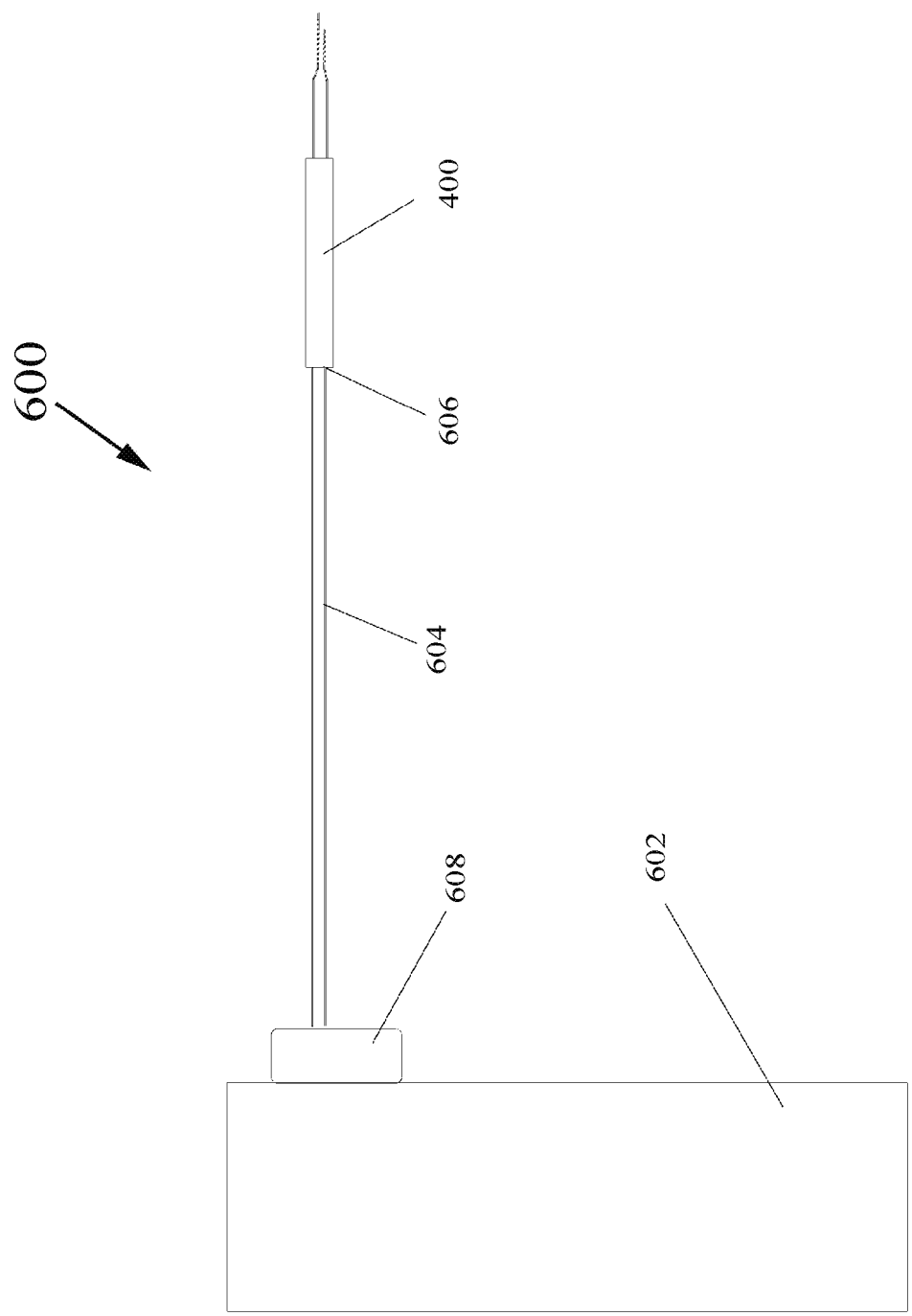
FIG. 6 is an embodiment of the invention interconnected with a console that houses a power supply and a cryogen source.

FIG. 6 depicts a multi-functional ablation device 600 of the invention with a dual ablation probe 400 detachable from an energy supply console 602. An umbilical 604 connects to the dual ablation probe 400 at a tight junction 606 and also to the console 602 at an easy-attach connection 608. This allows the dual ablation probe 400 to be attached to a number of energy sources. The console 602 houses an electric supply that has at least one source of hyperthermic energy including radiofrequency energy (RF), microwave energy, high frequency ultrasound energy (HiFU), laser light energy, or thermoelectric energy, alone or in combination. The console 602 houses a cryogen source that includes at least one of a thermoelectric module or a cryogenic fluid such that the cryogenic fluid is in a pressurized state, compressed liquid state, critical state, near critical state, or supercritical state. For exemplary purposes only and not limitation, supercritical nitrogen (SCN) systems, compressed liquid cryogen at its critical state, or pressurized argon systems may be utilized as the cryogen source.

Aspects of the system facilitate the use of multiple umbilicals where the sources of heat energy or cooling energy vary. The umbilical 604 is about 20 feet in length or less. Without limitation, however, the umbilical 604 may be any length up to about 35 feet or more as desired or practicable.

One embodiment of the invention uses an integral dual thermal ablation probe which delivers heat energy and cryogenic energy to a target tissue. The device is designed to increase tissue ablation through the co-application of heat and freezing to the target cancer tissue while reducing collateral damage to surrounding non-targeted tissues. This novel dual thermal ablation device allows for more effective, reproducible, and controllable tissue ablation to treat diseased tissue.

In addition to providing dual heat energy and cryogenic energy ablation modes within a single medical device, the system also provides for the integrated delivery and use of anti-cancer agents which work independently or in combination with either mode of treatment.

Operational use of the dual thermal ablation device allows for application of any combination of heating, freezing, or anti-cancer agent application to the target tissue. For exemplary purposes, use of the device to ablate a target tissue area on the skin comprises application of an anticancer agent to the target tissue, followed by freezing of the target, heating of the target, and then a final freeze. Other methods of application include, but are not limited to, procedures such as: freeze alone; heat alone; freeze/heat/freeze; heat/freeze/heat; agent/heat/freeze; agent freeze/agent/heat; or any combination of application of freezing, heating, and/or any number of anti-cancer agents.

The combination of treatment into a single modality supports the utilization of ablation techniques in personalized molecular medicine. The integral device results in more effective cell ablation of the target tissue with minimal damage to neighboring healthy tissue. The multi-functional probe or catheter is a hand-held, bench top or portable device that provides a physician easy and rapid access to real-time individual and/or combined application of heat energy, cryogenic energy, and/or administration of other medicinal therapy (e.g. anti-cancer agents).

One embodiment of the device is utilized for the target ablation of cardiac tissue. Various other embodiments utilize the device in the target ablation of tissues of the skin, esophagus, bladder, endometrium, breast, prostate, liver, heart, pancreas, lung, brain, and kidney. The invention delivers both heat energy and cryogenic energy to the application tip of a pen-like hand-held device, such as to the tip of a probe or catheter. Aspects of the invention also integrate a table top or modular unit with the associated probes or catheters.

Mechanisms for delivering the energy sources (i.e. hot or cold temperatures) include use of any combination of cascaded thermoelectric Peltier cooling and heating system, compressed gas (e.g. $CO_2$, $Ar_2$, or $N_2$) cooling, and/or resistance wire heating. Each approach generates probe tip temperatures for ablating undesirable tissue: Tip temperatures range between about +40° C. and +80° C. or greater (heat mode) and around about −40° C. to −80° C. or colder (freeze mode), depending on the energy source and configuration utilized. For instance, cryogenic energy produced temperatures less than about −40° C. which effectively ablates cancerous tissue. In one configuration, the multi-functional approach using Peltier cooling generates hyperthermic temperatures at the target site of about +40° C. to +50° C. and freeze mode temperatures of about −42° C. For exemplary purposes and not limitation, cryogenic cooling sources generate tip temperatures of about −70° C. to −80° C. or colder.

In another embodiment, the dual thermal ablation device comprises a configuration of a cryoablation system in combination with a thermal ablation device such as radiofrequency (RF), high frequency ultrasound, laser, thermal pellets, or any other approach to delivering heating and freezing in tandem to a target tissue.

As described, several configurations of the device are embodied in the invention including, but not limited to, $CO_2$ or resistance wire and thermoelectric (cascaded Peltier) heating and cooling. Several advantages of the system include efficiency, cost reduction, miniaturization capabilities, and reliability.

In conjunction with the multi-functional thermal device (heating and cooling mechanism), a series of ablation application tips have been developed. The tip configurations include, but are not limited to, about a 2.0 mm diameter×2.0 cm long needle, about a 1.5 mm diameter×1.0 cm long needle, about a 5.0 mm wide×1.0 cm long wedge, and about a 1.0 cm diameter paddle. These various tips provide for a variety of treatment approaches as integral with the heat energy delivery and/or cryogenic energy delivery.

Though the multi-functional ablation device has been described in terms of its preferred embodiments, the various embodiments and aspects of the invention may be utilized in various treatment procedures in a patient. The use of a multi-functional device benefits the treatment procedures of several organs and other tissues of a patient, including inter-tissue and surface ablation, ablation of tumors, and epicardial and endocardial ablation.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth here-below not be construed as being order-specific unless such order specificity is expressly stated in the claim.

What is claimed is:

1. A multi-functional ablation device comprising:
   a hybrid thermal-cooling system comprising an electrical power supply and a cryogen source, wherein said electrical power supply includes at least one of ultrasound energy, laser light energy, or thermoelectric energy;
   a longitudinal body having a proximal end and a distal end wherein said proximal end includes an outer sheath having an electrical connection contained therein and connected to said electrical power supply, and wherein said distal end is a closed tip with a thermally conductive surface;
   an ablation zone positioned within said distal end and defined by said thermally conductive surface;
   a cryogen supply line disposed through said longitudinal body and interconnected with said cryogen source for generating subzero temperatures;
   a wall having an inner surface and an outer surface such that said inner surface creates a cryogen return lumen surrounding said cryogen supply line and said outer surface creates an insulative lumen between said wall and said outer sheath, said wall extended circumferentially through said longitudinal body; and
   one or more heating elements lining an internal surface of said ablation zone of said distal end of said longitudinal body and contacting said thermally conductive surface of said closed tip, said one or more heating elements interconnected with said electrical connection of said longitudinal body for generating hyperthermic temperatures;
   wherein said ablation zone directs subzero temperatures and hyperthermic temperatures to said thermally conductive surface, and
   wherein said multi-functional ablation device is configured to provide heat ablation and cryoablation individually or in combination.

2. The multi-functional ablation device of claim 1, wherein said ablation zone is an integral unit configured for alternating use of said subzero temperatures and said hyperthermic temperatures.

3. The multi-functional ablation device of claim 1, wherein said ablation zone comprises one or more thermoelectric elements interconnected with said thermally conductive surface.

4. The multi-functional ablation device of claim 1, wherein said longitudinal body is a handheld device and configured to attach to said cryogen source or to said electrical power supply by way of an umbilical.

5. The multi-functional ablation device of claim 1, wherein said longitudinal body is a portable unit wherein said cryogen source is a cartridge positioned within said longitudinal body along with said electrical power supply.

6. The multi-functional ablation device of claim 1, wherein said insulative lumen is a vacuum.

7. The multi-functional ablation device of claim 1, wherein said insulative lumen comprises fiber materials including fiberglass, rock wool, slag wool, cellulose, natural fibers, rigid foam, or sleek foils.

8. The multi-functional ablation device of claim 1, wherein said cryogen source is a gas or liquid cryogen.

9. The multi-functional ablation device of claim 1, wherein said hyperthermic temperatures are in the range of between +40° C. to at least +80° C.; and said subzero temperatures are in the range of between −40° C. to −200° C. or colder.

10. The multi-functional ablation device of claim 9, wherein said subzero temperatures are in the range of between −80° C. to −140° C.

11. The multi-functional ablation device of claim 9, wherein said subzero temperatures are in the range of between −160° C. to −196° C.

12. The multi-functional ablation device of claim 1, wherein said one or more heating elements comprise resistance wire and a thermoelectric circuit.

13. The multi-functional ablation device of claim 1, wherein said outer sheath encapsulates said cryogen source and said electrical power supply.

14. The multi-functional ablation device of claim 1, wherein said longitudinal body is a probe or a catheter.

15. The multi-functional ablation device of claim 1, wherein
   said cryogen source comprises a thermoelectric module or a cryogenic fluid, wherein said cryogenic fluid is in a pressurized state, compressed liquid state, critical state, near critical state, or supercritical state.

16. The multi-functional ablation device of claim 15, wherein said cryogenic fluid is above a critical point temperature.

17. The multi-functional ablation device of claim 1, wherein said one or more heating elements includes a thermoelectric heater coil.

18. The multi-functional ablation device of claim 1, wherein said one or more heating elements includes a Peltier heating chip.

19. A multi-functional ablation device comprising:
   a hybrid thermal-cooling system comprising an electrical power supply and a cryogen source, wherein said electrical power supply includes at least one of ultrasound energy, laser light energy, or thermoelectric energy;
   a longitudinal body having a proximal end and a distal end wherein said proximal end includes an outer sheath having an electrical connection contained therein and connected to said electrical power supply, and wherein said distal end is a closed tip with a thermally conductive surface;

an ablation zone positioned within said distal end and defined by said thermally conductive surface;

a cryogen supply line disposed through said longitudinal body and interconnected with said cryogen source for generating subzero temperatures;

a wall having an inner surface and an outer surface such that said inner surface creates a cryogen return lumen surrounding said cryogen supply line and said outer surface creates an insulative lumen between said wall and said outer sheath, said wall extended circumferentially through said longitudinal body; and one or more heating elements lining an internal surface of said ablation zone of said distal end of said longitudinal body and contacting said thermally conductive surface of said closed tip, said one or more heating elements interconnected with said electrical connection of said longitudinal body for generating hyperthermic temperatures;

wherein said ablation zone directs subzero temperatures and hyperthermic temperatures to said thermally conductive surface.

\* \* \* \* \*